US006383734B1

(12) United States Patent
Marshall et al.

(10) Patent No.: US 6,383,734 B1
(45) Date of Patent: May 7, 2002

(54) METHOD TO DETERMINE INHIBITION OF PAK3 ACTIVATION OF RAF-1

(75) Inventors: Mark Steven Marshall, Carmel; Henry Bruce Diaz, Indianapolis; Alastair James King, Indianapolis; Huaiyu Sun, Indianapolis, all of IN (US)

(73) Assignee: Advanced Research and Technology Institute, Inc., Indianapolis, IN (US)

( * ) Notice: Subject to any disclaimer, the term of this patent is extended or adjusted under 35 U.S.C. 154(b) by 0 days.

(21) Appl. No.: 09/163,507

(22) Filed: Sep. 30, 1998

(51) Int. Cl.[7] .......................... C12Q 1/00; G01N 33/53; G01N 33/574
(52) U.S. Cl. .......................... 435/4; 435/7.1; 435/7.71; 435/7.23
(58) Field of Search .......................... 435/4, 7.1, 7.71, 435/7.23

(56) References Cited

U.S. PATENT DOCUMENTS

| 5,597,719 A | * | 1/1997 | Freed et al. | |
| 5,605,825 A | | 2/1997 | Abo et al. | 435/194 |
| 5,698,428 A | | 12/1997 | Abo et al. | 435/194 |
| 5,698,445 A | | 12/1997 | Abo et al. | 435/325 |

OTHER PUBLICATIONS

Bagrodia, S., et al., "Cdc–42 and PAK–Mediated Signaling Leads to Jun Kinases and p38 Mitogen–Activated Protein Kinase Activation", *Journal of Biological Chemistry*, 270, Abstract Only, 27995–8 (Nov. 1995).

Bagrodia, S., et al., "Identification of a Mouse p21^(Cdc42/Rac) Activated Kinase", *Journal of Biological Chemistry*, 270, 22731–22737 (Sep. 1995).

Benner, G.E., et al., "Activation of an S6/H4 Kinase (PAK 65) from Human Placenta by Intramolecular and Intermolecular Autophosphorylation", *Journal of Biological Chemistry*, 270, 21121–21126 (Sep. 1995).

Diaz, B., et al., "Phosphorylation of Raf–1 Serine 338–Serine 339 Is an Essential Regulatory Event for Ras–Dependent Activation and Biological Signaling", *Molecular and Cellular Biology*, 17, 4509–4516 (Aug. 1997).

Fabian, J.R., et al., "Critical Tyrosine Residues Regulate the Enzymatic and Biological Activity of Raf–1 Kinase", *Molecular and Cellular Biology*, 13, 7170–7179 (Nov. 1993).

King, A.J., et al., "Isolation of a c–RAF–1 Serine 338/339 Kinase Activity from Rat Spleen", Thirteenth Annual Meeting on Oncogenes, Abstract Only (1997).

King, A.J., et al., "Pak3 Positively Regulates Raf–1 Activity By Phosphorylation of the Serine 338–339 Site", *Oncogene* (1998).

King, A.J., et al., "The Protein Kinase Pak3 Positively Regulates Raf–1 Activity Through Phosphorylation of Serine 338", *Nature*, 396, Abstract Only, 180–3 (Nov. 1998).

Martin, G.A., et al., "A Novel Serine Kinase Activated by rac1/CDC42Hs–Dependent Autophosphorylation is Related to PAK65 and STE20", *EMBO Journal*, 14, 1970–1978 (May 1995).

Martin, G.A., et al., "A Novel Serine Kinase Activated by rac1/CDC42Hs–Dependent Autophosphorylation is Related to PAK65 and STE20—Correction", *EMBO Journal*, 14, 4385 (1995).

Morrison, D.K., et al., "Mechanisms Regulating Raf–1 Activity in Sibnal Transduction Pathways", *Molecular Reproduction and Development*, 42, 507–514 (1995).

Morrison, D.K., et al., "The Complexity of Raf–1 Regulation", *Current Opinion in Cell Biology*, 9, 174–179 (1997).

Tang, Y., et al., "A Role for Pak Protein Kinases in Schwann Cell Transformation", *Proc. Natl. Acad. Sci. U.S.A.*, 95, Abstract Only, 5139–5144 (Apr. 1998).

Tang, Y., et al., "Kinase–Deficient Pak1 Mutants Inhibit Ras Transformation of Rat–1 Fibroblasts", *Molecular and Cellular Biology*, 17, Abstract Only, 4454–4464 (Aug. 1997).

* cited by examiner

*Primary Examiner*—Anthony C. Caputa
*Assistant Examiner*—Gary B. Nickol
(74) *Attorney, Agent, or Firm*—Schwegman, Lundberg, Woessner & Kluth, P.A.

(57) ABSTRACT

A method is provided to determine the ability of a test compound to alter PAK activation of Raf-1 comprising: (a) contacting a polypeptide comprising the catalytic domain of a PAK with the test compound in the presence of Raf-1; and (b) measuring the extent of activation of Raf-1.

8 Claims, 9 Drawing Sheets

```
p37   ------KELIINEILVMK------
Pak1  NLQQQPKKELIINEILVMRENKNPNIVNYLDSYLVGDELWVVMEYLAGGS
Pak2  NLQQQPKKELIINEILVMRENKNPNIVNYLDSYLVGDELWVVMEYLAGGS
Pak3  NLQKQPKKELIINEILVMKELKNPNIVNFLDSYLVGDELFVVMEYLAGGS p37   ------SDNVLLGMEG
Pak1  LTDVVTETCMDEGQIAAVCRECLQALEFLHSNQVIHRDIKSDNILLGMDG
Pak2  LTDVVTETCMDEGQIAAVCRECLQALDFLHSNQVIHRDIKSDNILLGMDG
Pak3  LTDVVTETCMDEAQIAAVCRECLQALEFLHANQVIHRDIKSDNVLLGMEG p37   SVK------ALYLIATNGTPELQNPEK------
Pak1  SVKLTDFGFCAQITPEQSKRSTMVGTPYWMAPEVVTRKAYGPKVDIWSLG
Pak2  SVKLTDFGFCAQITPEQSKRSTMVGTPYWMAPEVVTRKAYGPKVDIWSLG
Pak3  SVKLTDFGFCAQITPEQSKRSTMVGTPYWMAPEVVTRKAYGPKVDIWSLG p37   ------ALYLIATNGTPELQNPEK------
Pak1  IMAIEMIEGEPPYLNENPLRALYLIATNGTPELQNPEKLSAIFRDFLNRC
Pak2  IMAIEMVEGEPPYLNENPLRALYLIATNGTPELQNPERLSAVFRDFLNRC
Pak3  IMAIEMVEGEPPYLNENPLRALYLIATNGTPELQNPEKLSPIFRDFLNRC p37   ------ELLQHPFLK------
Pak1  LEMDVEKRGSAKELLQHPFLKIAKPLSSLTPLIAAAKEATKNNH*
Pak2  LEMDVDRRGSAKELLQHPFLKLAKPLSSLTPLILAAKEAIKNSSR
Pak3  LEMDVEKRGSAKELLQHPFLKLAKPLSSLTPLILAAKEAMKSNR*
```

FIG. 3

SEQUENCE LISTING

<160> NUMBER OF SEQ ID NOS: 11

<210> SEQ ID NO 1
<211> LENGTH: 244
<212> TYPE: PRT
<213> ORGANISM: Rattus norvegicus

<400> SEQUENCE: 1

```
Asn Leu Gln Lys Gln Pro Lys Glu Leu Ile Ile Asn Glu Ile Leu
  1               5                  10                 15

Val Met Lys Glu Leu Lys Asn Pro Asn Ile Val Asn Phe Leu Asp Ser
             20                  25                  30

Tyr Leu Val Gly Asp Glu Leu Phe Val Val Met Glu Tyr Leu Ala Gly
             35                  40                  45

Gly Ser Leu Thr Asp Val Val Thr Glu Thr Cys Met Asp Glu Ala Gln
         50                  55                  60

Ile Ala Ala Val Cys Arg Glu Cys Leu Gln Ala Leu Glu Phe Leu His
 65                  70                  75                  80

Ala Asn Gln Val Ile His Arg Asp Ile Lys Ser Asp Asn Val Leu Leu
             85                  90                  95

Gly Met Glu Gly Ser Val Lys Leu Thr Asp Phe Gly Phe Cys Ala Gln
            100                 105                 110

Ile Thr Pro Glu Gln Ser Lys Arg Ser Thr Met Val Gly Thr Pro Tyr
            115                 120                 125

Trp Met Ala Pro Glu Val Val Thr Arg Lys Ala Tyr Gly Pro Lys Val
        130                 135                 140

Asp Ile Trp Ser Leu Gly Ile Met Ala Ile Glu Met Val Glu Gly Glu
145                 150                 155                 160

Pro Pro Tyr Leu Asn Glu Asn Pro Leu Arg Ala Leu Tyr Leu Ile Ala
            165                 170                 175

Thr Asn Gly Thr Pro Glu Leu Gln Asn Pro Glu Lys Leu Ser Pro Ile
            180                 185                 190

Phe Arg Asp Phe Leu Asn Arg Cys Leu Glu Met Asp Val Glu Lys Arg
            195                 200                 205

Gly Ser Ala Lys Glu Leu Leu Gln His Pro Phe Leu Lys Leu Ala Lys
        210                 215                 220

Pro Leu Ser Ser Leu Thr Pro Leu Ile Leu Ala Ala Lys Glu Ala Met
225                 230                 235                 240

Lys Ser Asn Arg

<210> SEQ ID NO 2
<211> LENGTH: 244
<212> TYPE: PRT
<213> ORGANISM: Rattus norvegicus

<400> SEQUENCE: 2

Asn Leu Gln Gln Gln Pro Lys Glu Leu Ile Ile Asn Glu Ile Leu
  1               5                  10                 15

Val Met Arg Glu Asn Lys Asn Pro Asn Ile Val Asn Tyr Leu Asp Ser
             20                  25                  30

Tyr Leu Val Gly Asp Glu Leu Trp Val Val Met Glu Tyr Leu Ala Gly
             35                  40                  45

Gly Ser Leu Thr Asp Val Val Thr Glu Thr Cys Met Asp Glu Gly Gln
         50                  55                  60

Ile Ala Ala Val Cys Arg Glu Cys Leu Gln Ala Leu Glu Phe Leu His
 65                  70                  75                  80

Ser Asn Gln Val Ile His Arg Asp Ile Lys Ser Asp Asn Ile Leu Leu
             85                  90                  95

Gly Met Asp Gly Ser Val Lys Leu Thr Asp Phe Gly Phe Cys Ala Gln
            100                 105                 110

Ile Thr Pro Glu Gln Ser Lys Arg Ser Thr Met Val Gly Thr Pro Tyr
            115                 120                 125
```

```
Trp Met Ala Pro Glu Val Val Thr Arg Lys Ala Tyr Gly Pro Lys Val
    130                 135                 140

Asp Ile Trp Ser Leu Gly Ile Met Ala Ile Glu Met Ile Glu Gly Glu
145                 150                 155                 160

Pro Pro Tyr Leu Asn Glu Asn Pro Leu Arg Ala Leu Tyr Leu Ile Ala
                165                 170                 175

Thr Asn Gly Thr Pro Glu Leu Gln Asn Pro Glu Lys Leu Ser Ala Ile
            180                 185                 190

Phe Arg Asp Phe Leu Asn Arg Cys Leu Glu Met Asp Val Glu Lys Arg
        195                 200                 205

Gly Ser Ala Lys Glu Leu Leu Gln His Gln Phe Leu Lys Ile Ala Lys
    210                 215                 220

Pro Leu Ser Ser Leu Thr Pro Leu Ile Ala Ala Lys Glu Ala Thr
225                 230                 235                 240

Lys Asn Asn His
```

<210> SEQ ID NO 3
<211> LENGTH: 245
<212> TYPE: PRT
<213> ORGANISM: Rattus norvegicus

<400> SEQUENCE: 3

```
Asn Leu Gln Gln Gln Pro Lys Lys Glu Leu Ile Ile Asn Glu Ile Leu
  1                 5                  10                  15

Val Met Arg Glu Asn Lys Asn Pro Asn Ile Val Asn Tyr Leu Asp Ser
                 20                  25                  30

Tyr Leu Val Gly Asp Glu Leu Trp Val Val Met Glu Tyr Leu Ala Gly
             35                  40                  45

Gly Ser Leu Thr Asp Val Val Thr Glu Thr Cys Met Asp Glu Gly Gln
 50                  55                  60

Ile Ala Ala Val Cys Arg Glu Cys Leu Gln Ala Leu Asp Phe Leu His
 65                  70                  75                  80

Ser Asn Gln Val Ile His Arg Asp Ile Lys Ser Asp Asn Ile Leu Leu
                 85                  90                  95

Gly Met Asp Gly Ser Val Lys Leu Thr Asp Phe Gly Phe Cys Ala Gln
                100                 105                 110

Ile Thr Pro Glu Gln Ser Lys Arg Ser Thr Met Val Gly Thr Pro Tyr
            115                 120                 125

Trp Met Ala Pro Glu Val Val Thr Arg Lys Ala Tyr Gly Pro Lys Val
    130                 135                 140

Asp Ile Trp Ser Leu Gly Ile Met Ala Ile Glu Met Val Glu Gly Glu
145                 150                 155                 160

Pro Pro Tyr Leu Asn Glu Asn Pro Leu Arg Ala Leu Tyr Leu Ile Ala
                165                 170                 175

Thr Asn Gly Thr Pro Glu Leu Gln Asn Pro Glu Arg Leu Ser Ala Val
            180                 185                 190

Phe Arg Asp Phe Leu Asn Arg Cys Leu Glu Met Asp Val Asp Arg Arg
        195                 200                 205

Gly Ser Ala Lys Glu Leu Leu Gln His Pro Phe Leu Lys Leu Ala Lys
    210                 215                 220

Pro Leu Ser Ser Leu Thr Pro Leu Ile Leu Ala Ala Lys Glu Ala Ile
225                 230                 235                 240

Lys Asn Ser Ser Arg
                245
```

<210> SEQ ID NO 4
<211> LENGTH: 15
<212> TYPE: PRT
<213> ORGANISM: Artificial Sequence
<220> FEATURE:
<223> OTHER INFORMATION: RAF-1 peptide

<400> SEQUENCE: 4

```
Arg Pro Arg Gly Gln Arg Asp Ser Ser Phe Phe Trp Glu Ile Glu
 1               5                  10                  15
```

<210> SEQ ID NO 5
<211> LENGTH: 27
<212> TYPE: DNA
<213> ORGANISM: Artificial Sequence
<220> FEATURE:
<223> OTHER INFORMATION: A primer

<400> SEQUENCE: 5
ggtggaattc agccgaaaac ccccgtg                                    27

<210> SEQ ID NO 6
<211> LENGTH: 30
<212> TYPE: DNA
<213> ORGANISM: Artificial Sequence
<220> FEATURE:
<223> OTHER INFORMATION: A primer

<400> SEQUENCE: 6
gcccctcgag ctagaagaca ggcagcctcg                                 30

<210> SEQ ID NO 7
<211> LENGTH: 14
<212> TYPE: PRT
<213> ORGANISM: Rattus norvegicus

<400> SEQUENCE: 7

```
Arg Pro Arg Gly Gln Arg Asp Ser Ser Tyr Tyr Trp Glu Ile
 1               5                  10
```

<210> SEQ ID NO 8
<211> LENGTH: 12
<212> TYPE: PRT
<213> ORGANISM: Rattus norvegicus

<400> SEQUENCE: 8

```
Lys Glu Leu Ile Ile Asn Glu Ile Leu Val Met Lys
 1               5                  10
```

<210> SEQ ID NO 9
<211> LENGTH: 13
<212> TYPE: PRT
<213> ORGANISM: Rattus norvegicus

<400> SEQUENCE: 9

```
Ser Asp Asn Val Leu Leu Gly Met Glu Gly Ser Val Lys
 1               5                  10
```

<210> SEQ ID NO 10
<211> LENGTH: 18
<212> TYPE: PRT
<213> ORGANISM: Rattus norvegicus

<400> SEQUENCE: 10

-continued

```
Ala Leu Tyr Leu Ile Ala Thr Asn Gly Thr Pro Glu Leu Gln Asn Pro
1               5                   10                  15

Glu Lys

<210> SEQ ID NO 11
<211> LENGTH: 9
<212> TYPE: PRT
<213> ORGANISM: Rattus norvegicus

<400> SEQUENCE: 11

Glu Leu Leu Gln His Pro Phe Leu Lys
1               5
```

METHOD TO DETERMINE INHIBITION OF PAK3 ACTIVATION OF RAF-1

One of the most remarkable advances in cell biology has been the continuing clarification of the signaling pathway by which mitogens, after binding on the cell surface receptors, transmit into the nucleus the signals which trigger de novo synthesis of DNA and mitosis. See, for example, R. J. Davis, *J. Biol. Chem.*, 268, 14553 (1993). All components of this pathway are not identical in all cell types. However, the transmission of developmental and proliferative signals from the membrane to the nucleus requires the coordinated action of a diverse set of proteins. As shown in FIG. 1, the mitogen-signaling pathway typically includes receptor tyrosine kinases, the Src family of nonreceptor tyrosine kinases, Ras, Raf-1, MEK (MKK), MAPK, and RSK.

FIG. 1 also depicts two members of the Rho subclass of GTP-binding proteins, Rac and Cdc42, which are believed to target and activate the p21 -activated family of serine/threonine protein kinases called PAKs (p21-activated kinases). E. Manser et al., *Nature*, 367, 40 (1994).

The Raf-1 serine/threonine kinase serves as a control intermediate in these pathways, functioning both as a link between membrane-bound and cytoplasmic proteins and as a bridge connecting upstream tyrosine kinases such as EGF or PDGF receptors with downstream serine/threonine kinases. Both the essential role and the position of Raf-1 in many signaling pathways have been demonstrated from studies using deregulated and dominant inhibitory Raf-1 mutants in mammalian cells as well as from studies employing biochemical and genetic techniques in *Xenopus laevis*, *Drosophila melanogaster*, and *Caenorhabditis elegans* (reviewed in T. M. Roberts, *Nature*, 360, 534 (1992)). In many cases, the activation of Raf-1 by receptors that stimulate cellular tyrosine phosphorylation is dependent on the activity of Ras, indicating that Ras functions upstream of Raf-1 (K. W. Wood et al., *Cell*, 68, 1041 (1992)). Upon activation, Raf-1 then phosphorylates and activates MEK (MKK), resulting in the propagation of the signal to downstream effectors, such as MAPK (mitogen-activated protein kinase) (C. M. Crews et al., *Cell*, 74, 215 (1993)).

Deregulation of the Ras signaling cascade can result in oncogenic cellular transformation through the constitutive activation of one or more downstream effectors. J. Bas, *Cancer Res.*, 49, 4682 (1989); M. S. Marshall, *FASEB J.*, 9, 134 (1995). Although a growing number of signaling proteins have been implicated as being subject to direct activation by Ras-GTP, the Raf serine/threonine kinases are considered to be the primary Ras effectors involved in the proliferation of animal cells. J. Avruch et al., *Trends Biochem. Sci.*, 19, 279 (1994); C. M. Crews et al., cited above.

Normally localized in the cytosol in an inactive form, Raf-1 associates with Ras at the plasma membrane following growth factor-induced Ras guanine nucleotide exchange. S. Traverse et al., *Oncogene*, 8, 3175 (1993). Genetically engineered Raf-1, localized to the plasma membrane through posttranslational modification with myristate or isoprenoid, is active in the absence of Ras-GTP. This observation suggests that Ras functions primarily as a plasma membrane docking protein (G. Heidecker et al., *Mol. Cell. Biol.*, 10, 2503 (1990); S. J. Leevers et al., *Nature*, 369, 411 (1994); D. Stokoe et al., *Science*, 264, 1463 (1994)). Once at the membrane, Raf-1 becomes catalytically activated through a complex and still largely undefined mechanism. These activation steps probably include both phosphorylation and a conformational change which relieves the inhibition imposed by the Raf-1 amino terminus (P. T. Dent et al., *Science*, 8, 1902 (1995); G. Heidecker et al., *Adv. Cancer Res.*, 58, 53 (1992); D. K. Morrison, *Molec. Reprod. Dev.*, 42, 507 (1996)). Lastly, lipid factors may bind to partially activated Raf-1, resulting in full activation. (See, Dent et al., cited above.)

Raf-1 activation requires phosphorylation, since treatment of active Raf-1 with protein phosphatases specific for either phosphoserine or phosphotyrosine results in loss of kinase activity (P. T. Dent et al., *Science*, 268, 1902 (1995); T. Jelinek et al., *Mol. Cell. Biol.*, 16, 1027 (1996)). Raf-1 is predominantly phosphorylated in vivo on serines 43, 259, and 621 (D. K. Morrison, *Mol. Reprod. Biol.*, 42, 507 (1996)). Phosphorylation of serines 43 and 259 has negative regulatory functions related to inhibition by protein kinase A and 14.3.3 binding. Serine 621 appears to have multiple roles. It is essential for Raf activation, but phosphorylation of this residue by protein kinase A or Raf-1 itself is associated with down regulation of Raf kinase activity (H. Mischak et al., *Mol. Cell. Biol.*, 16, 5409 (1996)).

Potential inducible activators of Raf include protein kinase Cα (PKCα) and Src family tyrosine kinases (W. Kolch et al., *Nature*, 364, 249 (1993)). PKCα phosphorylates Raf-1 on serine 499 (S499), which results in stimulation of catalytic activity in vitro. However, the in vitro activation of Raf-1 by membranes from cells transformed by Ras and Src does not require either S499 or PKCα (S. G. MacDonald et al., *Mol. Cell. Biol.*, 13, 1615 (1993)). A more definitive regulatory role has been demonstrated for the Src-dependent tyrosine phosphorylation of Raf-1 residues 340 and 341 (J. R. Fabian et al., *Mol. Cell. Biol.*, 13, 7120 (1993); R. Marais et al., *EMBO J.*, 14, 3136 (1995)). Phosphorylation of tyrosine 340 and 341 (Y340 and Y341) strongly activates the kinase and transforming activities of full-length Raf-1. v-Src-dependent phosphorylation of Raf-1 Y340-Y341 has been shown to be dependent upon colocalization of Raf-1 with Ras-GTP at the plasma membrane. However, replacement of Y340 and Y341 with phenylalanine has no effect on the ability of a truncated Raf-1 CR3 fragment to transform fibroblasts, although v-Src-dependent phosphorylation dramatically increases the catalytic activity of this fragment. Furthermore, the physiological significance of Y340 and Y341 phosphorylation is uncertain since phosphotyrosine is difficult to detect on Raf-1 activated by growth factors in mammalian tissue culture.

Recently, it was demonstrated that phosphorylation of Raf-1 serine 338-serine 339 is an essential regulatory event for Ras-dependant activation and further biological signaling. B. Diaz et al., *Mol. Cell. Biol.*, 17, 4509 (1997). The authors proposed that Raf-1 residues 338 to 341 constitute a unique site of coordinate serine and tyrosine phosphorylation and that this is one of several key events which occur only at the plasma membrane. A. J. King et al. reported isolation of a kinase activity capable of phosphorylating c-Raf-1 on serine 338/339 from rat spleen. The kinase was found to have a molecular weight of about 60 kD, and was insensitive to PKC and PKA inhibitors. Abstracts, 13th Ann. Meeting on Oncogenes, Frederick, Mo. (Jun. 18–21, 1997); Abstracts, 14th Ann. Meeting on Oncogenes, San Diego, Calif. (Jun. 24–27, 1998). However, the actual mechanism and consequences of these events remains unknown.

SUMMARY OF THE INVENTION

The present invention provides a method to determine the ability of a test compound to alter PAK3 activation of Raf-1 by contacting a polypeptide comprising the catalytic domain of PAK3 (p21-activated protein kinase) with the test compound in the presence of Raf-1 and measuring the extent of activation of Raf-1, by phosphorylation in vitro or in vivo. Because the activation of Raf-1 triggers downstream events in the MAPK signaling pathway that can lead to cellular proliferation, test compounds will typically be screened for their ability to inhibit PAK3 activation of Raf-1, i.e., to inhibit the ability of a PAK3 species to phosphorylate Raf-1 serine 338. The inhibition of PAK3 thus inhibits the resultant protein kinase activity of Raf-1 and, as a consequence, blocks activation of the whole downstream cascade, including the pivotal activation of MAPK. For example, see J. Wie et al., Science, 262, 1065 (1993) and J. Marx, Science, 262, 988 (1993).

Compounds that inhibit PAK3 activation of Raf-1 can modulate the mitogen cellular signaling pathway and provide treatments for neoplasia, lymphoproliferative disorders, arthritis, inflammation, autoimmune diseases, apoptosis and the like.

The term Raf-1 as used herein includes isolated and purified native and recombinant mammalian isoforms of Raf-1, as well as subunits (fragments), variants and analogs of Raf-1, such as Raf-1 CR3, that can be evaluated for phosphorylation and/or in growth/proliferation assays. Such variants, subunits and analogs conserve Ser 338 and, preferably, adjacent N-terminal amino acids.

Abo et al. (U. S. Pat. No. 5,605,825) have disclosed that identification of agents that modify the interaction of the human PAK1 species, hPAK65, with the rho-like p21 GTPases rac1 and CDC42H, may alter the activation of hPAK65. Abo et al. do not disclose or suggest a method to identify agents that can directly modify, i.e., inhibit the ability of PAK3 to phosphorylate and thus, to activate, Raf-1. It is not known if regulation of Raf-1 by PAK3 is dependant on either Cdc42 or Rac in vivo.

BRIEF DESCRIPTION OF THE FIGURES

FIG. 3. Tryptic peptide microsequencing of p37. Following large-scale purification of the 37-kD kinase from 40 g of rat spleen, four tryptic peptides (SEQ ID NO:8, SEQ ID NO:9, SEQ ID NO:10 and SEQ ID NO:11 were analyzed by mass spectrometric microsequence (MSMS) (analysis using a Finnigan LCQ Quadrupole Ion Trap Mass Spectrometer. The sequences derived from these four peptides were examined using the SWISS-PROT protein database and all showed absolute identity with PAK3. Interestingly, all of these sequences were located within the catalytic domain of PAK3. Some of the peptides shared identity with other PAK isoforms, PAK1, PAK2, but only where they themselves are homologous with PAK3. All sequences shown represent the rat isoforms.

Figure 1:
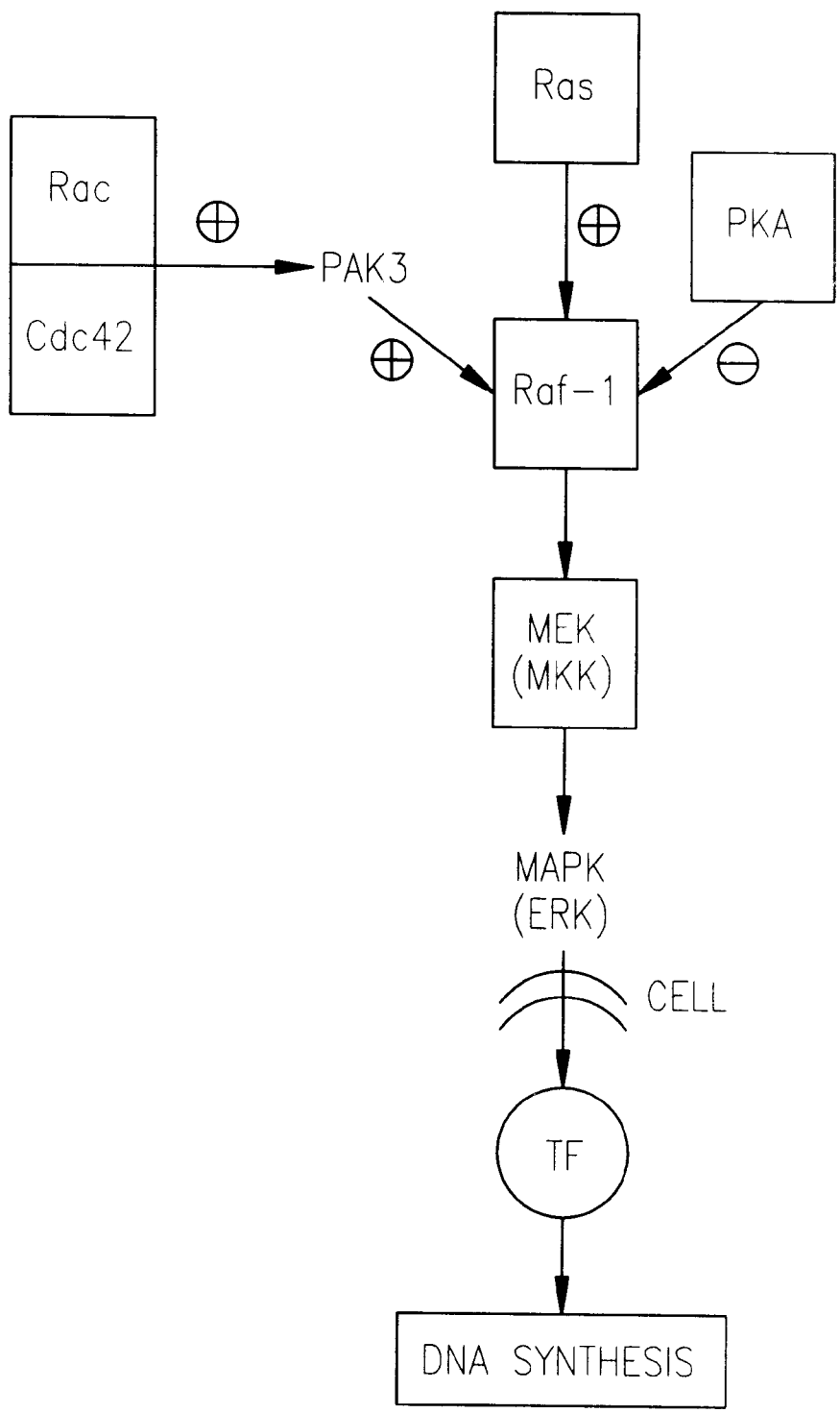
FIG. 1 is a schematic depiction of the mitogen-activated Ras pathway for transmitting cell growth signals, wherein (+) indicates activation of the next step and (−) indicates inhibition; MAPK: mitogen-activated protein kinase; MEK (MKK): mitogen-activated protein kinase kinase; Raf-1: a protein kinase; PKA: cAMP-dependent protein kinase A; PAK: p21-activated kinase; MEK: MAP kinase kinase; TF: transcription factors.

The effect of the same dominant negative mutant of PAK3 was tested for its ability to inhibit activation of Raf-1 kinase activity in response to oncogenic Ras$^{[V12]}$ (a, middle panel). This was further corroborated by the inability of dominant negative PAK3$^{[R278]}$ to inhibit the activation of the Raf-1 $^{[D338,E339]}$ mutant protein by Ras (a, right panel), where prior phosphorylation of the 338/339 site is imitated by acidic amino acid substitution. (b) Levels of PAK3 expression from Western blotting are shown below the graphs. Results are representative of three experiments. (c) Constitutively active PAK3$^{[S91,A93,A95]}$ (PAK3$^{ca}$) stimulated the kinase activity of both wild type Raf-1 and Raf-1$^{[A339]}$ proteins in transient transfections, but completely failed to activate the Raf-1$^{[A338]}$ mutant, indicating specificity for serine 338 in vivo. Results are normalized to the stimulation seen with Raf-1 in the presence of Ras$^{[V12]}$. (d) Raf-1 phosphorylated on serine 338 was immunoprecipitated from COS-7 cell lysates using a phosphoserine 338-specific antibody, detected by immunoblotting with 9E10 antibody and normalized to the amount of total myc-Raf-1 expressed in total cell lysates. Both Ras$^{[V12]}$ and PAK3$^{ca}$ elevated levels of serine 338 phosphorylation on Raf-1. A reduction in phosphoserine 338 was not detectable with the dominant negative PAK3$^{[R278]}$ (PAK3$^{dn}$) protein. These results are representative of four separate experiments.

DETAILED DESCRIPTION OF THE INVENTION

The present invention is based on the discovery that the rat kinase activity p37 that phosphorylates cRaf-1 on serine 338 is a truncated PAK3 (FIG. 3, SEQ ID NO:1) comprising the enzymatically active catalytic domain, and that PAK-3 phosphorylates Raf-1 on serine 338 in vitro and in vivo. Thus, the term "polypeptide comprising the catalytic domain of PAK3" includes isolated native mammalian PAK3 as well as subunits, analogs and variants of mammalian PAK3 that retain the ability to phosphorylate Raf-1, as determined by the assays herein. This includes the kinase domain (amino acids 230 . 507) and the subunit of rat PAK3 depicted in FIG. 3 which represents amino acid residues 281–524 (carboxy terminus of mature PAK3). See M. Teo et al., *J. Biol. Chem.*, 270, 26690 (1995). The full sequence of human PAK3 has been previously identified by G. A. Martin et al., *EMBO J.*, 14, 1970 (1995); *EMBO J.*, 14, 4385 (1995) and G. E. Benner et al., *J. Biol. Chem.*, 270, 21121 (1995). FIG. 3 also discloses truncated rat PAK-1 (SEQ ID NO:2) and PAK-2 (SEQ ID NO:3). Other PAK3 species and subunits thereof which can be employed in the present screening assay are disclosed, for example, in FIG. 2 of S. Bagrodia et al., *J. Biol. Chem.*, 270, 22731 (1995) as mouse PAK3 (mPAK-3).

It is believed that the PAK1 and PAK2 family members can also be used in the present assay, since the catalytic domains are highly conserved between family members. Rat PAK1 is disclosed by E. Manser et al., *Nature*, 367, 40 (1994) and in Bagrodia et al., FIG. 2, as rat p65PAK. Rat p65PAK is a PAK1 that is 81% identical to mouse PAK3 disclosed by Bagrodia et al. and is 98% identical in amino acid sequence to the human homolog hPAK-1. Human PAK2 is 78% identical to rat p65PAK. Other subunits of hPAK65 are disclosed in claim 1 of Abo et al. (U.S. Pat. No. 5,605,825) (see claim 1,(c),(d)). The complete amino acid sequence of hPAK65 shares only about 73% identity to rat p65PAK isolated from rat brain by Manser et al., though the catalytic domains are highly conserved. Both native PAK1 and PAK2 are also activated by proteolysis. R. D. Rooney et al., *J. Biol. Chem.*, 5 271, 21498 (1996); T. Rudel et al., *Science*, 226, 1571 (1997).

Sequence data and nomenclature for PAK1–3 are summarized in Table I, below.

TABLE I

Mammalian Pak Family Serine/Threonine Kinases*

Pak1

| | |
|---|---|
| Human | 545 amino acids, Accession #'s Q13153, Q13567 Pak-α EC 2.7.1.-, p65-Pak, p21-activated kinase, alpha-Pak |
| Rat | 544 amino acids, Accession #'s P35465, Q62934 Pak-α EC 2.7.1.-, p68-Pak, p21-activated kinase, alpha-Pak, protein kinase Muk2 |

TABLE I-continued

Mammalian Pak Family Serine/Threonine Kinases*

Pak2

| | |
|---|---|
| Rat | 544 amino acids, Accession # Q62829 Pak-β EC 2.7.1.-, p65-Pak, p21-activated kinase 2, beta-Pak |
| Mouse | 544 amino acids, Accession # Q61036 Pak-β EC 2.7.1.-, p21-activated kinase 2, p21-activated kinase-3, Pak-3, Stk4, beta-Pak |

Pak3

| | |
|---|---|
| Human | 524 amino acids, Accession #'s Q13177, Q13154 Pak-γ EC 2.7.1.-, p21-activated kinase 3, Pak65, S6/H4 kinase, Pak2, gamma-Pak |
| Rabbit | 524 amino acids, Accession # Q29502 Pak-γ EC 2.7.1.-, p21-activated kinase 3, p21-activated protein kinase I, PakI, gamma-Pak |
| Rat | 524 amino acids, Accession # Q64303 Pak-γ EC 2.7.1.-, p21-activated kinase 3, p62-Pak, gamma-Pak |

*Data taken from SWISS-PROT database.
http://expasy.hcuge.ch/sprot/
Human (homo sapiens), Rat (rattus norvegicus), Mouse (mus musculus) and Rabbit (oryctolagus cuniculus) sources as indicated.
Alternate names are given at the end of each entry.

Isolated variants of mammalian PAK3 useful in the present method have amino acid sequences that correspond to a PAK having at least 70% amino acid sequence identity (with increasing preference for sequences with at least 85%, 90%, 95%, 99%, to having one amino acid difference) to the corresponding native PAK3 sequence. Preferably, the isolated PAK3 (or PAK1 or 2 protein) exhibits 100% sequence identity to the corresponding catalytic domains shown in FIG. 3, i.e., in SEQUENCE ID NOS:1–3. The isolated proteins of the invention can be expressed using the polynucleotides such as those referenced or disclosed herein, operably linked to an appropriate control sequence in an expression vector suitable for expression in either a mammalian, insect, yeast, or bacterial cell.

The term "isolated or purified polypeptide or protein" referred to herein means a polypeptide or protein of cDNA, recombinant RNA, or synthetic origin or some combination thereof, which by virtue of its origin (1) is not associated with proteins found in nature, (2) is free of other proteins from the same source, e.g., free of human proteins, (3) is expressed by a cell from a different species, or (4) does not occur in nature.

The term "polypeptide" is used herein as a generic term to refer to native protein, fragments, variants or analogs of a polypeptide sequence. Hence, native protein, fragments, variants and analogs are species of the polypeptide genus. Preferred p21-interacting PAK3 polypeptides include: the rat truncated sequence comprising the polypeptide sequence shown in FIG. 3.; polypeptides comprising a kinase domain, such as those consisting essentially of a shaded sequence shown in FIG. 3, i.e., polypeptides consisting essentially of amino acids 300–344 of FIG. 3.

The term "native" or "naturally occurring" as used herein as applied to a compound refers to the fact that the compound can be found in nature. For example, a polypeptide or polynucleotide sequence that is present in an organism (including viruses) that can be isolated from a source in nature, and which has not been intentionally modified by man in the laboratory, is naturally occurring.

The term "sequence homology" or "sequence identity" referred to herein describes the percentage or proportion of amino acid matches between two amino acid sequences.

When sequence homology is expressed as a percentage, e.g., 50%, the percentage denotes the proportion of matches over the length of sequence from a given PAK that is compared to some other sequence.

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching and are treated as mismatches between the sequence; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of more than 5 (in standard deviation units) using the program ALIGN with the mutation data matrix and a gap penalty of 6 or greater. See Dayhoff, M. O., in Atlas of Protein Sequence and Structure, 1972, volume 5, National Biomedical Research Foundation, pp. 101–110, and Supplement 2 to this volume, pp. 1–10. The two sequences or parts thereof are more preferably homologous if their amino acids are greater than or equal to 50% identical when optimally aligned using the ALIGN program.

As used herein, the twenty conventional amino acids and their abbreviations follow conventional usage (Immunology—A Synthesis, 2nd Edition, E. S. Golub and D. R. Gren, Eds., Sinauer Associates, Sunderland, Mass. (1991)). In the polypeptide notation used herein, the left-hand direction is the amino terminal direction and the right-hand direction is the carboxy-terminal direction, in accordance with standard usage and convention. Stereoisomers (e.g., D-amino acids) of the twenty conventional amino acids, unnatural amino acids such as $\alpha,\alpha$-disubstituted amino acids, N-alkyl amino acids, lactic acid, and other unconventional amino acids such as lactic acid, may also be suitable components for polypeptides used in the present assay. Examples of unconventional amino acids include: 4-hydroxyproline, $\gamma$-carboxyglutamate, $\epsilon$-N,N,N-trimethyllysine, $\epsilon$-N-acetyllysine, O-phosphoserine, N-acetylserine, N-formylmethionine, 3-methylhistidine, 5-hydroxylysine, $\omega$-N-methylarginine, and other similar amino acids and imino acids (e.g., 4-hydroxyproline).

Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acid substitution groups are: valine-leucine-isoleucine, phenylalanine-tyrosine, lysine-arginine, alanine-valine, glutamic-aspartic, and asparagine-glutamine.

The term "polypeptide fragment or subunit" as used herein refers to a polypeptide that has an amino-terminal and/or carboxy-terminal deletion, but where the remaining amino acid sequence is identical to the corresponding positions in the naturally occurring sequence deduced, for example, from a full-length cDNA sequence. Fragments typically are at least 5, 6, 8 or 10 amino acids long, preferably at least 14 amino acids long, more preferably at least 20 amino acids long, usually at least 50 amino acids long, and even more preferably at least 70 amino acids long.

The term "variant or analog" as used herein refers to polypeptides which comprise a segment of at least 25 amino acids that has substantial identity to a portion of the deduced amino acid sequence shown in FIG. 3 and which has at least one of the following properties: (1) serine protein kinase activity, or (2) ability to modulate Raf-1 activity. Typically, variant polypeptides comprise a conservative amino acid substitution (or addition or deletion) with respect to the naturally occurring sequence. Variants typically are at least 20 amino acids long, preferably at least 50 amino acids long or longer, most usually being as long as SEQ ID NO:1 or full-length naturally occurring PAK3 polypeptide. Analogs preferably contain unconventional amino acid residues, including derivatized amino acids and linkages other than amido.

In addition to polypeptides consisting only of naturally occurring amino acids, PAK analogs known as peptidomimetics are also provided. Peptide analogs are commonly used in the pharmaceutical industry as non-peptide drugs with properties analogous to those of the template peptide. These types of non-peptide compounds are termed "peptide mimetics" or "peptidomimetics" (J. Fauchere, *Adv. Drug Res.*, 15, 29 (1986); Veber and Freidinger, *TINS*, p. 392 (1985); and Evans et al., *J. Med. Chem.*, 30, 1229 (1987), which are incorporated herein by reference) and are usually developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human PAK3, but have one or more peptide linkages optionally replaced by a linkage selected from the group consisting of: —$CH_2NH$—, —$CH_2S$—, —$CH_2$—$CH_2$—, —$CH=CH$— (cis and trans), —$COCH_2$—, —$CH(OH)CH_2$—, and —$CH_2SO$—, by methods known in the art and further described in the following references: A. F. Spatola in "Chemistry and Biochemistry of Amino Acids, Peptides and Proteins," B. Weinstein, eds., Marcel Dekker, New York, p. 267 (1983); A. F. Spatola, Vega Data (March 1983), Vol. 1, Issue 3, "Peptide Backbone Modifications" (general review); J. S. Morley, *Trends Pharm. Sci.*, pp. 463–468 (1980) (general review).

Systematic substitution of one or more amino acids of a consensus sequence with a D-amino acid of the same type (e.g., D-lysine in place of L-lysine) may be used to generate more stable peptide analogs. In addition, constrained peptides comprising a consensus sequence or a substantially identical consensus sequence variation may be generated by methods known in the art (Rizo and Gierasch, *Ann. Rev. Biochem.*, 61, 387 (1992), incorporated herein by reference); for example, by adding internal cysteine residues capable of forming intramolecular disulfide bridges which cyclize the peptide.

The term "test compound" is used herein to denote a chemical compound, a mixture of chemical compounds, a biological macromolecule, or an extract made from biological materials such as bacteria, plants, fungi, or animal (particularly mammalian) cells or tissues. Agents are evaluated for potential activity as PAK3/Raf-1 modulatory agents (e.g., antineoplastic agents, cytotoxic agents, inhibitors of neoplastic transformation or cell proliferation, cell proliferation-promoting agents, Raf-induced tumorigenicity, and the like) by inclusion in screening assays described herein.

The term "candidate agent" is used herein to refer to an agent which is identified by one or more screening method (s) of the invention as a putative human modulatory agent of the mitogen activated cellular signaling pathway. Some candidate modulatory agents have therapeutic potential as drugs for human use.

The term "antineoplastic agent" is used herein to refer to agents that have the functional property of inhibiting a development or progression of a neoplasm or neoplastic cell growth in a human, particularly a malignant (cancerous) lesion, such as a carcinoma, sarcoma, lymphoma, or leukemia. Inhibition of metastasis is frequently a property of antineoplastic agents.

It can be advantageous to employ a peptide analog of native PAK3, or a portion thereof, as a pharmaceutical agent or as a commercial research reagent. For example, a peptide analog of PAK3 having high affinity for Raf-1 can be used as a competitive inhibitor of Raf-1 activation by competing with native PAK3 for binding to Raf-1. A peptide analog of Raf-1 that can bind to PAK3 could also be used in this fashion.

Thus, the PAKs described herein, particularly PAK3 can be used to alter PAK3/Raf-1 pathways and associated disease conditions, and to identify agents that effect or modulate PAK3 activity and related pathways. Such PAK modulating agents can provide novel chemotherapeutic agents for treatment of neoplasia, lymphoproliferative conditions, arthritis, angiogenesis, inflammation, autoimmune diseases, apoptosis, and the like.

For example, agents which alter Raf-1/PAK3 interactions or interfere with PAK3 kinase activity in neoplastic and/or preneoplastic cells may be developed as potential human therapeutic drugs. Candidate antineoplastic agents may be identified by their ability to inhibit activation of Raf-1 by PAK3 in vitro and/or in vivo and/or inhibit PAK3 protein kinase function in vitro and/or in vivo (e.g., block the ability of PAK3 to phosphorylate cellular targets downstream in a Raf-1-dependent pathway). Accordingly, methods of identifying antineoplastic and immunomodulatory agents are provided by the invention.

Candidate antineoplastic agents are then tested further for antineoplastic activity in assays which are routinely used to predict suitability for use as human antineoplastic drugs. Examples of these assays include, but are not limited to: (1) ability of the candidate agent to inhibit the ability of anchorage-independent transformed cells to grow in soft agar, (2) ability to reduce tumorigenicity of transformed cells transplanted into nu/nu mice, (3) ability to reverse morphological transformation of transformed cells, (4) ability to reduce growth of transplanted tumors in nu/nu mice, (5) ability to inhibit formation of tumors or preneoplastic cells in animal models of spontaneous or chemically induced carcinogenesis, and (6) ability to induce a more differentiated phenotype in transformed cells to which the agent is applied.

Compounds which inhibit PAK3 activity may serve as immunomodulatory agents, for example, to treat, block or attenuate an inflammatory reaction, graft-versus-host reaction, or autoimmune condition, neurodegenerative disease, and the like.

In some embodiments, it is desirable to compare the structure of PAK3 protein to the structure of other proteins. This will aid in the identification of and selection of drugs that either selectively affect PAK3 or have a broad-spectrum effect on more than one species of related polypeptide (e.g., other PAK related proteins). In one embodiment of the invention, an assay for determining PAK3 protein kinase activity is provided.

In another embodiment of the invention, a PAK3 kinase inhibition assay is provided, which assay can be used for screening drug libraries or agents for their capability to inhibit a PAK3 kinase activity. In one embodiment of this invention, a method is provided for identifying agents which inhibit PAK3 kinase activity, said method comprising administering an agent to a reaction mixture containing substantially purified PAK, preferably activated PAK, a substantially purified substrate, e.g., MBP, and $\gamma$-$^{33}$P-ATP, and then determining the extent to which the agent inhibits phosphorylation of substrate as compared to a control reaction lacking the agent.

Accordingly, also provided is an assay kit for identifying agents which inhibit PAK3 kinase activity wherein the kits contain substantially purified polypeptide containing PAK3, or more preferably constitutively activated PAK3 or a fragment thereof with constitutive activity. Activated PAK3 can be provided in numerous forms including as the autophosphorylated form, as an analog having at least one autophosphorylation-target serine replaced by an amino acid that mimics phosphoserine, e.g., Glu or Asp (Huang et al., Proc. Natl. Acad. Sci., 91, 8960–8963 (1994)), and as an N-terminal truncated form in which the PAK3 regulatory domain responsible for inhibiting serine kinase activity is deleted. The assay kit can further contain a substantially purified substrate, such as MBP, and can further contain a buffered aqueous solution and $\gamma$-$^{33}$P-ATP.

A further embodiment of the invention is an in vitro or in vivo assay in which a test compound is contacted with a polypeptide comprising the catalytic domain(s) of a PAK, i.e., PAK3 in the presence of Raf-1 or a phosphorylatable analog thereof, preferably in the presence of Ras. The ability of PAK3 to phosphorylate Raf-1 serine 338 is measured in the presence or absence of the test compound. Preferably, the PAK3 polypeptide is activated by incubation with activated GTPase prior to carrying out this assay or other kinase assays.

Posphorylation of Raf-1 can be detected using preparations of polyclonal or monoclonal antibodies which bind to a Raf-1 epitope comprising phosphorylated Ser-338. Such antibodies can be made by immunizing a mammal with an immunogenic phosphopeptide comprising the Raf-1-derived epitope or moiety S(P*)S, i.e., SEQ ID NO:7.

In order for compounds that inhibit (or modulate) PAK3 phosphorylation of Raf-1 activity or one of its other activities to be therapeutically useful, they should be active on intact mammalian cells. Several methods are readily available for determining the activity of candidate PAK3 inhibitors (or modulators) against PAK3 phosphorylation of Raf-1 on intact cells. Phosphorylation of the Raf-1 can be measured using antiphosphoserine antibodies or phosphopeptide fingerprints. Also, additional intracellular signaling events can be measured including calcium flux, cellular proliferation, and cellular DNA synthesis, or any of the other physiological processes related to Raf-1/Ras dependent pathways. Preferably, a cell line genetically engineered to express constitutively active PAK3, Raf-1 and preferably Ras may lead to a transformed cell line upon which candidate inhibitors can be tested for the ability to decrease Raf-1 activation, decrease overall phosphorylation in a cell, or to revert the cell to a less transformed state. For example, phosphorylated Raf-1 can be immunoprecipitated from COS-7 cells transfected with myc-tagged Raf-1, RasV 12 and various PAK3 constructs, disclosed hereinbelow. The resolved phosphorylated tagged Raf-1 can be detected on PVDF by reacting it with a commercially available antibody against myc, such as 9E10.

Therapeutically active compounds identified by the assay of the present invention can be administered to a mammalian host in a variety of forms, i.e., they may be combined with various pharmaceutically acceptable inert carriers in the form of tablets, capsules, lozenges, troches, hard candies, powders, sprays, elixirs, syrups, injectable or eye drop solutions, and the like depending on the chosen route of administration, e.g., orally or parenterally. Parenteral administration in this respect includes administration by the following routes: intravenous, intramuscular, subcutaneous, intraocular, intrasynovial, transepithelial (including transdermal, ophthalmic, sublingual and buccal), topical (including ophthalmic, dermal, ocular, rectal, nasal or oral inhalation via insufflation and aerosol), and rectal.

The invention will be further described by reference to the following detailed examples, which employed the following methodologies.

A. Purification of kinase from rat spleen. Cytosolic extracts were prepared from frozen rat spleens (8–10 g) by repeated homogenization in a low osmotic potential buffer (10 mM Tris-HCl, 50 mM NaF, 5 mM MgCl$_2$, 1 mM EGTA, 1 mM DTT, 250 µM Na$_3$VO$_4$, 4 µg/ml leupeptin, 4 µg/ml pepstatin A, 10 µg/ml aprotinin, 10 µg/ml soybean trypsin inhibitor, 3 mM PMSF, 1 mM benzamidine-HCl, pH 7.5). The extract was made up to 50 mM NaCl prior to column chromatography at 4° C. whereafter Raf-1 serine 338/339 kinase was successively resolved over heparin-Agarose, Blue-Sepharose, Sephacryl HiPrep S-200, Mono-Q and Mono-P matrices. Fractions were assayed for Raf-1 peptide phosphorylation (see below for assay). Kinase samples were analyzed with Raf-CR3, to confirm phosphorylation of Raf-1 serine 338/339, as described below.

B. Kinase assays. Kinase samples were assessed for their ability to phosphorylate 500 µM Raf-1 peptide ($_{33}$, RPRGQRDSSFFWEIE$_{345}$) (SEQ ID NO:4) in the presence of 500 µMATP (containing 2 µCi [γ-$^{32}$P]-ATP at 30° C. for 10 minutes. Incubations were analyzed by P-81 phosphocellulose paper assay. Phosphorylation of serine 338/339 in Raf-CR3 was determined by similar incubations containing 1 µg of substrate at 30° C. for 30–60 minutes. Proteins were resolved by SDS-PAGE, transferred to Immobilon-P and the dried, Ponceau S-stained membranes were autoradiographed. Raf-1 kinase activity was measured by the coupled assay method using GST-Mek 1, GST-Erk1 and myelin basic protein by the method of D. Stokoe et al., *Science*, 264, 1463 (1994).

C. In-gel kinase assay. Using the method of Chao et al., *J. Biol. Chem.*, 269 7337 (1994), kinase extracts were resolved by SDS-PAGE on 10% (w/v) acrylamide low cross-linker gels (29.5% w/v acrylamide, 0.5% w/v bis-acrylamide) with 200 µg/ml myelin basic protein in one half of the gel; the other half incorporated buffer only. Gel segments were equilibrated with pre-warmed kinase assay buffer (25 mM HEPES-NaOH, 10 mM MgCl$_2$, 5 mM 2-mercaptoethanol, 90 µM Na$_3$VO$_4$, pH 7.4) then incubated with 20 ml of buffer containing 250 µM ATP and 375 µCi [γ-$^{32}$P]-ATP at 30° C. for 60–90 minutes. Segments were washed repeatedly in 10 mM sodium pyrophosphate, 5% (w/v) trichloroacetic acid until no more radioactivity was released. Following silver staining of the no-substrate segment to locate protein bands, all segments were dried and autoradiographed (M. Eschenbauch et al., *Anal. Biochem.*, 125, 96 (1982)).

D. Expression of recombinant Raf-CR3 in *E. Coli*. DNA sequences encoding residues 307–648 of human c-Raf-1 were amplified by polymerase chain reaction using the 5'-primer GGTGGAATTCAGCCGAAAAC-CCCCGTG (SEQ ID NO:5) and the 3'-primer GCCCCTCGAGCTAGAAGACAGGCAGCCTCG (SEQ ID NO:6). The amplified DNA was purified, digested with EcoRI and XhoI and cloned into the Stratagene pCAL-n vector. The entire Raf-CR3 coding sequence was verified by termination reaction PCR DNA sequencing. Raf-CR3 D338E339 and A338A339 substitution mutants were generated by site-directed mutagenesis using the Promega Altered SitesTM in vitro mutagenesis system. Raf-CR3-calmodulin binding protein fusions were expressed in *E. coli* strain BL21 (pLysS). Bacteria were induced at 30° C. with 0.5 mM IPTG and Raf-CR3 was recovered over calmodulin-Sepharose using the Stratagene protocol.

E. 2-D phosphopeptide mapping and phosphoamino acid analysis.

Phosphorylated Raf-CR3 was mapped by the method of Boyle et al., *Met. in Enzymol.*, 201, 110 (1991). Raf-CR3 was resolved by SDS-PAGE, recovered and oxidized. It was then dissolved in 100 mM NH$_4$HCO$_3$, pH 8.3 and digested twice with TPCK-treated trypsin at 37° C. Phosphopeptides were recovered and electrophoresed on cellulose thin layer plates (Merck 5716) in 1% (w/v) (NH$_4$)$_2$CO$_3$, pH 8.9 at 1000 V for 25 minutes. Plates were chromatographed in the second dimension in 37.5% (v/v) n-butanol, 25% (v/v) pyridine, 7.5% (v/v) acetic acid at room temperature for 7.5 hours, dried and autoradiographed.

Immunoprecipitations were also carried out from digests using a rabbit polyclonal antibody raised against human Raf-1 residues 337–354 to identify the serine 338/339 phosphopeptide. Peptides were eluted from beads with 7.8% (v/v) acetic acid, 2.2% (v/v) formic acid (pH 1.9 buffer), lyophilized repeatedly from water and mapped as described. Phosphoamino acid analysis was performed as described by Boyle et al., cited above, except that samples were only resolved in one dimension by electrophoresis.

F. Transfections. COS-7 cells were transfected with 10 µg of each plasmid DNA (pcEXV3 containing Ras$^{[V12]}$, myc-Raf, myc-Raf-CX or pJ3H containing PAK3) by electroporation. Cells were lysed three days post-transfection in the presence of protease and phosphatase inhibitors and Raf-1 kinase activity was then examined as described by Stokoe et al., cited above. Transfection/expression efficiencies were assessed by densitometric scanning of Western blots of immunoprecipitates as well as cell lysates and data sets were normalized accordingly.

G. GTPase activation of kinase activity. GST-Rac1 and GST-Cdc42 (90 pg) were charged with 0.8 mM GTP$_γ$S using 50 µl glutathione-Sepharose beads as described by S. Bagrodia et al., *J. Biol. Chem.*, 270, 22731 (1995). GTP$_γ$S binding was achieved by incubation for 25 minutes at 30° C. Proteins were eluted from the beads by incubation with 160 µl buffer containing 100 mM glutathione, pH 7.5 at 4° C. for 15 minutes. Supernatants were recovered for use in kinase activation assays. Briefly, 10 µl of kinase sample were incubated with 5 μg of activated GTPase at 4° C. for 60 minutes. Substrate and [γ-$^{32}$P]-ATP were then added and kinase assays were conducted as described above.

H. Immunological detection of Raf-1 containing phosphoserine 338. Rabbits were immunized with the KLH-conjugated phosphopeptide RPRGQRDS(P*)SYYWEI (SEQ ID NO:7) Bleeds were collected at week 10 and pooled. Antibodies were affinity purified over a phosphopeptide column and then passed over a non-phosphorylated peptide column to remove antibodies specific for the non-phosphorylated peptide. Preparations of monoclonal antibodies can also be prepared using standard hybridoma techniques.

Using the purified antibody, Raf-1 (phosphorylated on serine 338) was immunoprecipitated from COS-7 cells transfected with myc-tagged Raf-1, RasV12 and various PAK3 constructs. 5.5 μg of antibody were used per 100 μg of lysate protein and samples were incubated at 4° C. for 4 hours. Immune complexes were captured on Protein A-Sepharose beads for 3.5 hours. The immunoprecipitates were washed four times with lysis buffer then solubilized in SDS-PAGE sample buffer.

Immunoprecipitates from equal amounts of lysate (60 μg) were resolved on 8% SDS-polyacrylamide gels and proteins were transferred to PVDF membranes. myc-Raf-1 present in each immunoprecipitate, corresponding to the serine 338-phosphorylated population, was visualized by probing with the anti-myc (9E10) antibody. Relative expression levels of myc-Raf-1 were determined by running equal amounts of total lysate protein from each transfection on a parallel gel, transferring to PVDF and probing with the 9E10 antibody.

EXAMPLE 1

Isolation of PK Phosphorylation Activity from Rat Spleen

Figure 2A:
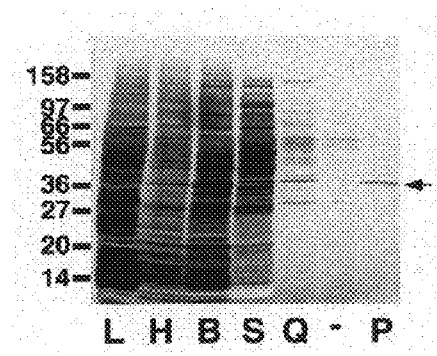
FIG. 2. Raf-1 serine 338/339 kinase was purified from rat spleen by sequential chromatography and identified as a specific Raf-1 serine 338/339 kinase. (a) The kinase was purified to virtual homogeneity when examined by silver-stained SDS-PAGE, with a molecular weight of 37 kD. Protein samples examined were crude spleen lysate (L), heparin-Agarose (H), Blue Sepharose (B), Sephacryl Hi-Prep S-200 (S), Mono-Q (Q) and Mono-P (P) eluates. Molecular weight standard sizes are shown in kD. (b) In-gel kinase assay using myelin basic protein as the substrate indicated kinase activity at molecular weights of 37 kD and 40 kD in both Mono-Q (Q) and Mono-P (P) extracts, confirming the 37-kD protein band as a bona fide protein kinase. (c) Phosphorylation of the serine 338/339 site in Raf-1 was confirmed using Raf-CR3 (WT) as the kinase substrate and compared with Raf-CR3$^{[D338,E339]}$, a non-phosphorylatable mutant (Mut). Only the wild type protein was significantly phosphorylated by highly purified (Q) or near homogeneous (P) samples of rat spleen Raf-1 serine 338/339 kinase. (d) Phosphorylated Raf-CR3 contained only phosphoserine by phosphoamino acid analysis, even after considerable autoradiograph exposure times. (e) 2-dimensional tryptic phosphopeptide mapping illustrated the presence of one phosphopeptide spot cluster, previously determined to comprise serine 338/339-containing peptides. B. Diaz et al., Mol. Cell. Biol., 17, 4509 (1997). Thin layer electrophoresis (TLE) and thin layer chromatography (TLC) dimensions are indicated. (f) This was confirmed by immunoprecipitation of the phosphopeptides using a rabbit polyclonal antibody raised against Raf-1 residues 337–354. Control samples are indicated throughout (C).

A survey of various rat organs suggested that the spleen contained the greatest abundance of a protein kinase activity capable of serine phosphorylation of a synthetic peptide corresponding to Raf-1 residues 331–345. This Raf-1 serine 338/339 protein kinase activity was purified from the cytosolic fraction of rat spleen homogenates using heparin-Agarose, Blue-Sepharose, Sephacryl Hi-Prep S-200, Mono-Q and Mono-P resins (FIG. 2a). The kinase eluted from Sephacryl Hi-Prep S-200 was resolved, using Mono-Q, into three major peaks of Raf-1 peptide kinase activity.

Only one of these peptide kinase activities was specific for the Raf-1 serine 338/339 site, as shown by 2-D phosphopeptide mapping of recombinant Raf-1 catalytic fragment (Raf-CR3) following phosphorylation by each separate activity. The active kinase fraction was further purified by isocratic elution from Mono-Q and finally resolved by isoelectric focusing over a Mono-P column. The protein kinase activity eluted with an isoelectric point of 5.95 and consisted of a near homogeneous 37-kD molecular weight protein, termed p37, as assessed by silver-stained SDS-PAGE (FIG. 2a, sample P). This was reflected in the extremely high specific activity (19,500 pmol/min/mg) achieved, representing a 6132-fold purification.

Figure 2B:
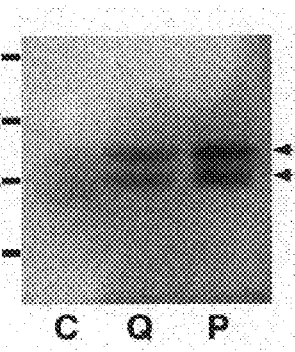
Figure 2C:
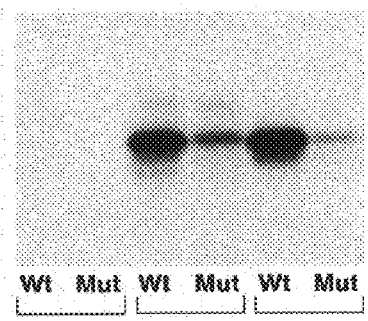

The purified Raf-1 serine 338/339 protein kinase was subjected to an in-gel kinase assay, using myelin basic protein as the substrate, which showed two reproducible bands of kinase activity (FIG. 2b). The presence of a 37-kD band confirmed the identity of the purified p37 as a protein kinase. The 40-kD activity, also faintly visible by silver stain in sample P of FIG. 2a, was later shown to be immunologically identical to the p37 protein kinase (see below). The specificity of the purified protein kinase for Raf-1 serine 338/339 was again confirmed using Raf-CR3 and Raf-CR3$^{[D338E339]}$, which lacks a phosphorylatable 338/339 site, as substrates (FIG. 2c). The purified kinase phosphorylated the wild type Raf-CR3 but failed to significantly phosphorylate the Raf-CR3$^{[D338E339]}$ mutant.

Figures 2D, 2E, 2F:
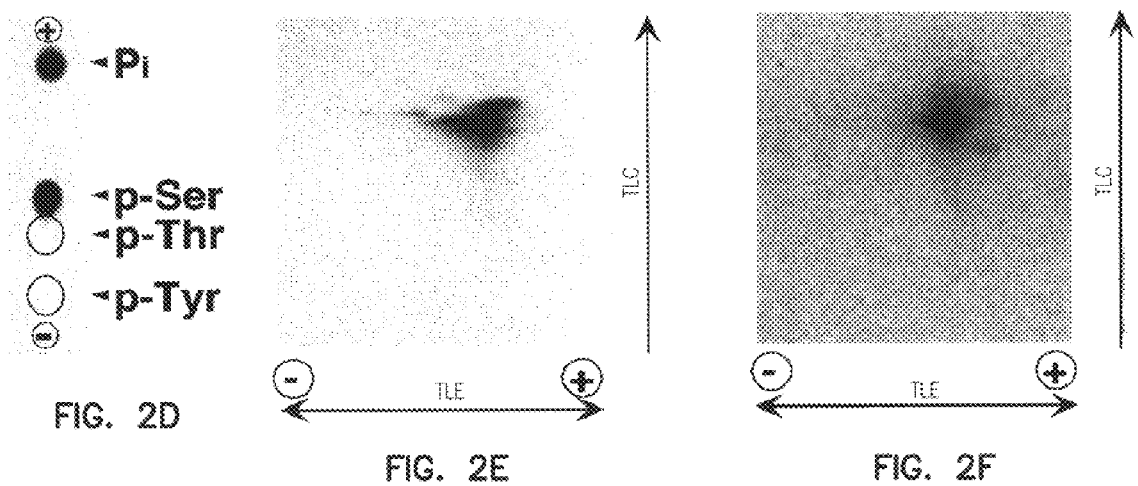

Phosphoamino acid analysis of the phosphorylated Raf-CR3 protein identified only phosphoserine (FIG. 2d). 2-D phosphopeptide mapping of Raf-CR3 phosphorylated by the purified protein kinase identified the same tryptic phosphopeptides previously shown to contain serine 338/339 (FIG. 2e). See, B. Diaz et al., Mol. Cell. Biol., 17, 4509 (1997). Over 95% of the $^{32}$P incorporated within the phosphorylated Raf-CR3 was associated with the serine 338/339 tryptic peptides. Phosphopeptide mapping of the Raf-CR3$^{[D338E339]}$ mutant protein from parallel kinase incubations revealed only the weakly phosphorylated background peptides also found in phosphorylated wild type Raf-CR3 (data not shown).

Phosphorylation of the serine 338/339 site was further verified by specific immunoprecipitation of the serine 338/339 tryptic phosphopeptides generated from phosphorylated Raf-CR3 using a polyclonal antibody raised against residues 337–354 of Raf-1. Immune, but not pre-immune, serum precipitated the major phosphopeptides found in the total tryptic digest, confirming serine 338/339 as the site of specific phosphorylation within Raf-CR3 (FIG. 2f). The occurrence of multiple phosphopeptides correlating with serine 338/339 phosphorylation has previously been explained in terms of incomplete tryptic cleavage and the possible heterogeneous phosphorylation of the two serine residues present.

EXAMPLE 2

Sequencing of 37 kD Protein

Having confirmed the specificity of the purified kinase for residues 338/339 of Raf-1, the purified 37-kD protein was identified by protein microsequencing. p37 obtained from a large-scale preparation was eluted from a preparative polyacrylamide gel, fragmented by digestion with trypsin and four of the HPLC-purified polypeptides were sequenced by mass spectrometric microsequence analysis. The amino acid sequences of these polypeptides were compared with the SWISS-PROT protein sequence database entries and were found to give a complete match with regions of the catalytic domain of the p21-activated protein kinase isoform PAK3 (FIG. 3). Hence, from the sequences obtained, it can be deduced that the purified 37-kD Raf-1 serine 338/339 protein kinase is a proteolytically cleaved catalytic domain of PAK3. Immunoblot analysis of the S338-specific Mono-Q peak with an antibody directed towards the C-terminus of PAK3, confirmed that both the 37 and 40 kilodalton kinase activities are proteolytic degradation fragments of full-length PAK3 which originated during purification. These PAK-3 polypeptides can also be useful in the present assay.

EXAMPLE 3

Phosphorylation of Raf-1

Figure 4A:
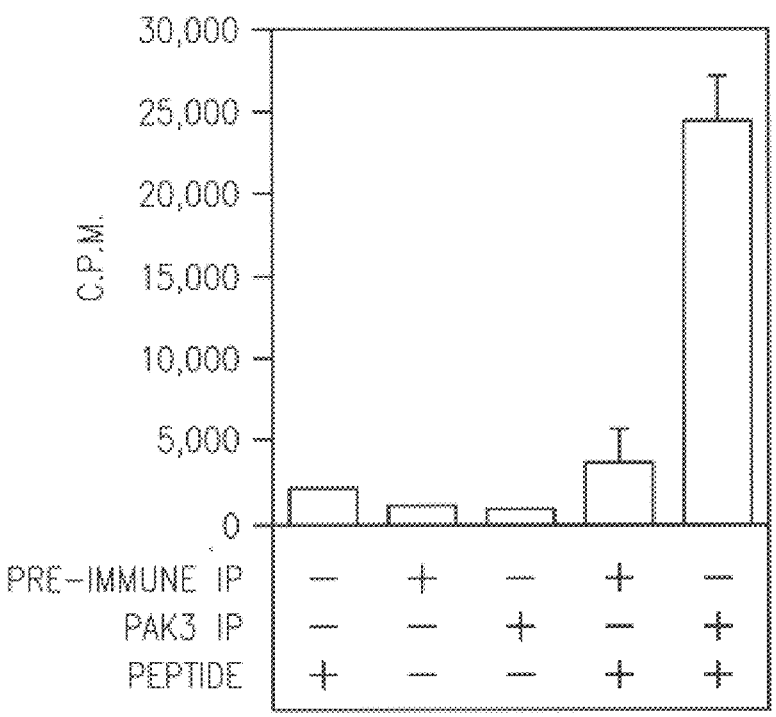
FIG. 4. Immunoprecipitated PAK3 and recombinant PAK3 were examined for their abilities to phosphorylate the Raf-1 peptide and Raf-CR3. (a) PAK3 was immunoprecipitated directly from rat spleen lysates using a C-terminal polyclonal antibody and was shown to phosphorylate the Raf-1 (331–345) peptide. (b) Immunoprecipitated PAK3 also phosphorylated wild type Raf-CR3. Specificity was demonstrated by the reduced ability of immunoprecipitated PAK3 to phosphorylate the Raf-CR3$^{[A338,A339]}$ or Raf-CR3 $^{[D338,E339]}$ mutant proteins. The pre-immune immunoprecipitate showed no significant kinase activity in either case. Results are representative of at least 3 experiments. (c) Recombinant His-tagged mouse PAK3 from Sf9 cells phosphorylated the Raf-1 peptide and this activity was stimulated in the presence of either Rac-GTP$_\gamma$S or Cdc42-GTP$_\gamma$S. (d) Recombinant His-tagged mouse PAK3 also strongly phosphorylated wild type Raf-CR3, but not Raf-CR3$^{[A338]}$, demonstrating specificity for the 338 site in vitro. This activity was again shown to be stimulated by Rac-GTP$_\gamma$S or Cdc42-GTP$_\gamma$S.

Following identification of PAK3 as the likely Raf-1 serine 338/339 kinase from rat spleen, the ability of full-length PAK3 to phosphorylate Raf-1 serine 338/339 when it was immunoprecipitated directly from rat spleen lysates was tested. Immunoprecipitates prepared with either an anti- PAK3 antibody or a pre-immune serum were initially assessed for kinase activity with the Raf-1 (331–345) peptide (FIG. 4a). This Raf-1 peptide analog is useful in the practice of the present assay method.

Figure 4B:
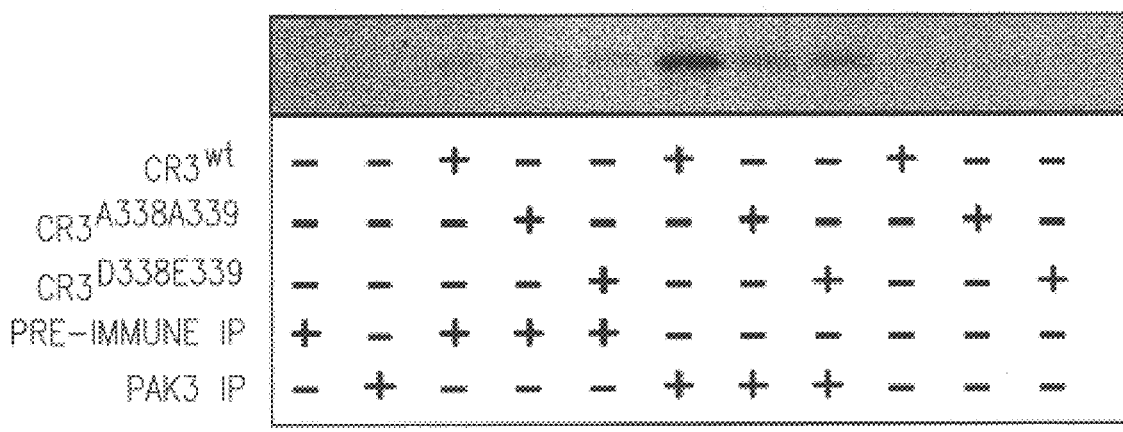
Figure 4C:
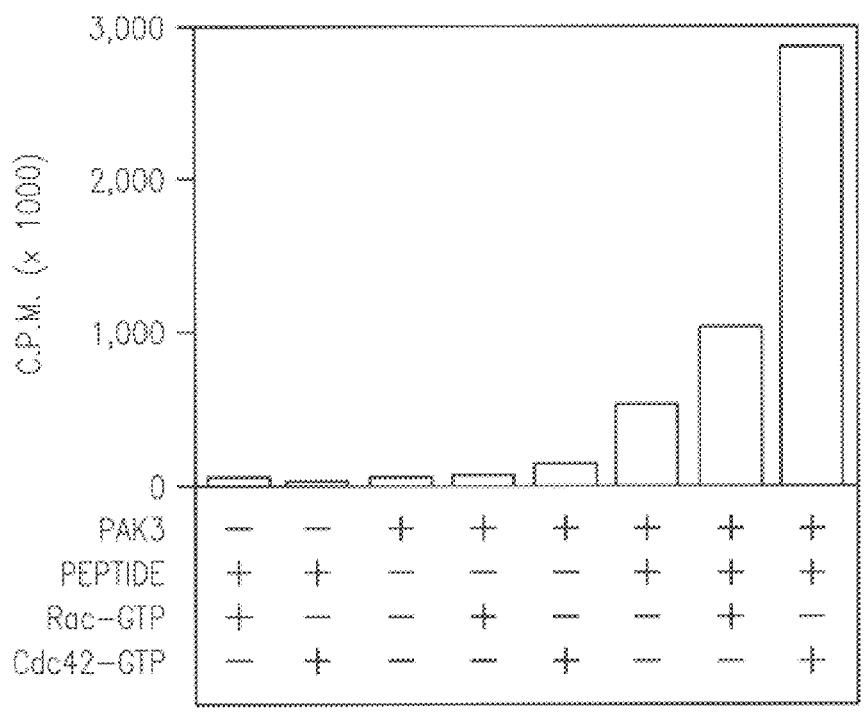
Figure 4D:
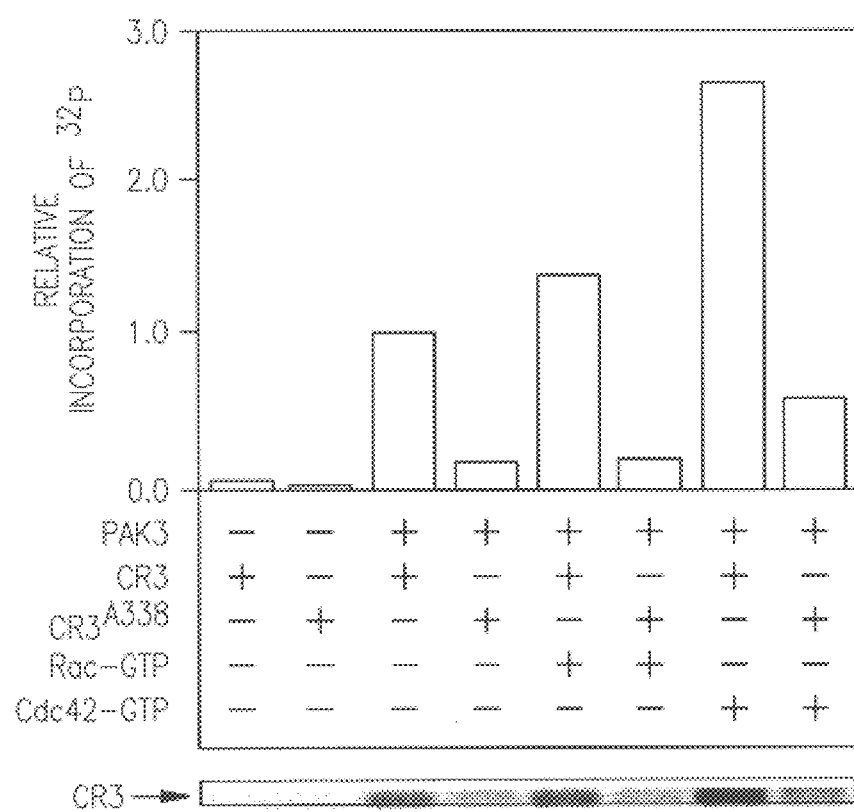

Immunoprecipitated PAK3 was subsequently shown to be capable of incorporating 4-fold more phosphate into wild type Raf-CR3 than into the non-phosphorylatable Raf-CR3 $[D338E339]$ or Raf-CR3$[A338A339]$ site mutants (FIG. 4b). Recombinant PAK3 prepared from Sf9 cells gave almost identical results to the immunoprecipitated PAK3, where the Raf-1 peptide and Raf-CR3 serine 338/339 kinase activity of the recombinant PAK3 was stimulated up to six-fold by co-incubation with GST-Rac-GTPγS or GST-Cdc42-GTPγS (FIGS. 4c and 4d). These results confirmed the identity of the purified Raf-1 serine 338/339 kinase in the purified preparations as a catalytic fragment of PAK3, rather than an undetected minor protein species. Immunodepletion of purified kinase with PAK3-specific antibodies removed kinase activity in a manner linearly proportional to the amount of protein immunoprecipitated from these samples (data not shown).

EXAMPLE 4

In vivo Regulation of Raf-1

Figure 5A:
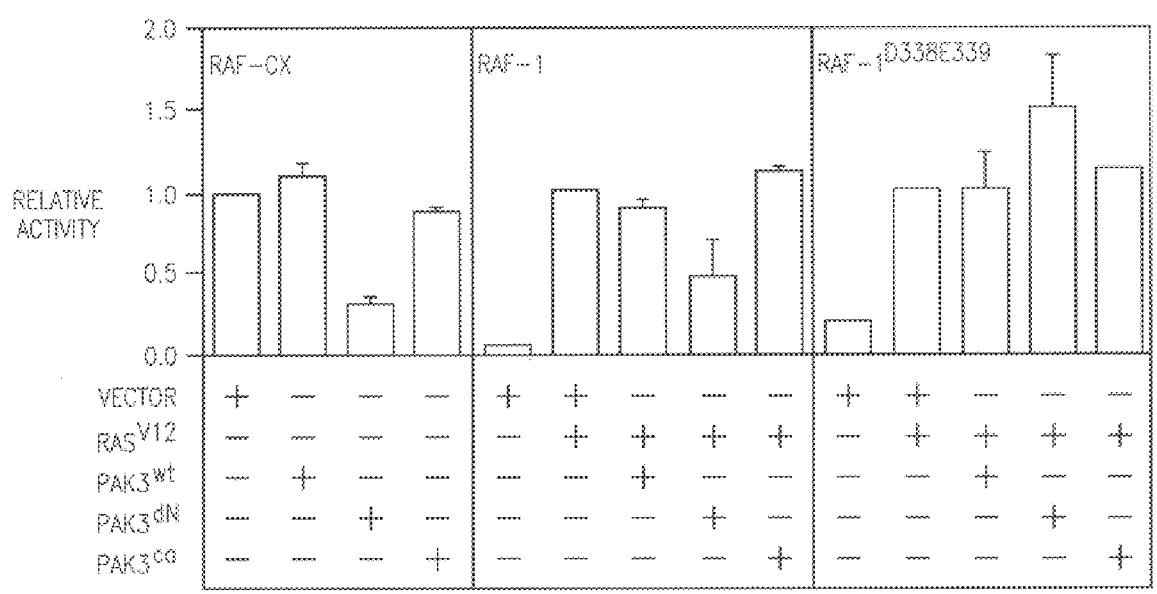
FIG. 5. The effect of PAK3 on Raf-1 activation in vivo was assessed in COS-7 cells. Plasmid constructs expressing different forms of HA-tagged PAK3 were transiently co-transfected with Raf-1 into COS-7 cells. The inhibitory effect of dominant negative PAK3$^{[R278]}$ (PAK3$^{dn}$) on the latent activation of Raf-CX (Raf modified to translocate to the plasma membrane independently of Ras), compared with the wild type (PAK3$^{wt}$) and the constitutively active PAK3 $^{[S91,S93,A95]}$ (PAK3$^{ca}$) mutant, is clearly visible (a, left panel).
Figure 5B:

In the light of this finding, tests were carried out to determine if PAK3 has an in vivo role in the regulation of Raf-1 activity through the direct phosphorylation of serine 338/339. The activity of the constitutive Raf-CX mutant, as well as wild type Raf-1 co-expressed with Ras$[V12]$, has been reported to be dependent upon phosphorylation of serine 338 and to a lesser extent serine 339. Wild type PAK3, the dominant negative PAK3$[R278]$ and the constitutively active PAK3$[S91,A93,A95]$ mutants were co-transfected with either Raf-CX, or Raf-1 together with Ras$[V12]$, into COS-7 cells and the effects on Raf kinase activity were measured (FIG. 5a). The dominant negative PAK3$[R278]$ mutant reduced both the intrinsic activity of Raf-CX (>70%; FIG. 5a left panel) as well as the Ras$[V12]$-inducible activation of Raf-1 (>50%; FIG. 5a middle panel) in transient transfections.

It has been previously demonstrated by Diaz et al., cited above, that substitution of serines 338 and 339 with aspartic acid and glutamic acid (which mimic phosphorylated residues) results in a Raf-1 protein which retains Ras$[V12]$-inducibility. Significantly, the dominant negative PAK3$[R278]$ mutant failed to inhibit the activation of a Raf-1 $[D338E339]$ mutant by Ras$[V12]$ (FIG. 5a right panel). The dominant negative PAK3$[R278]$ mutant can exert its effect only if there are phosphorylatable serine residues at serines 338 and 339 in Raf-1. This is powerful biochemical evidence for the direct in vivo regulation of Raf-1 by PAK3 through the phosphorylation of serine 338/339. Co-expression of wild type PAK3 or constitutively active PAK3$[S91,A93,A95]$ did not significantly increase the degree of Raf-CX or Ras$[V12]$-inducible Raf-1 activation, as has been similarly reported for similar PAK1 mutants in a biological assay system by Y. Tang et al., *Mol. Cell. Biol.*, 17, 4454 (1997).

Figure 5C:
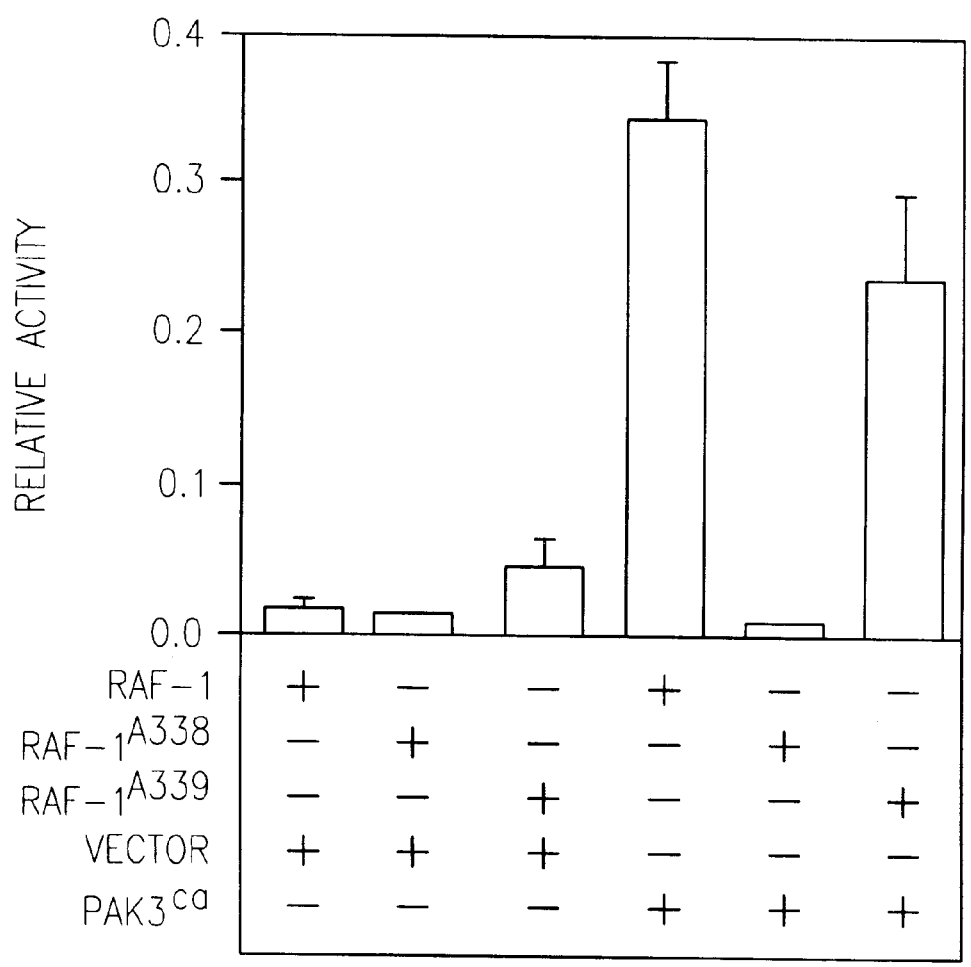
Figure 5D:
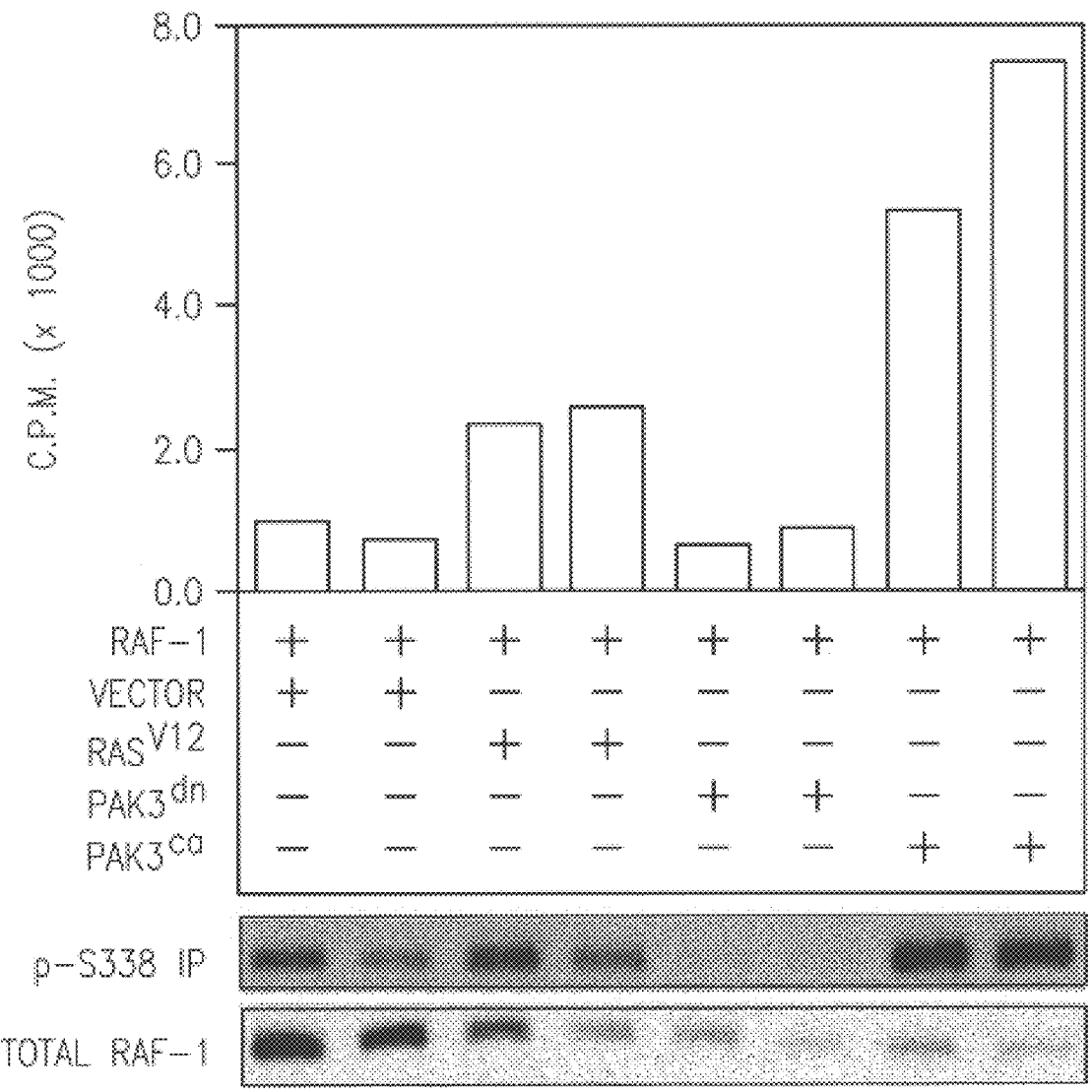

In the absence of Ras$[V12]$, the constitutively active PAK3 $[S91,A93,A95]$ mutant stimulated Raf-1 activity to nearly one third the level of oncogenic Ras$[V12]$ stimulation (FIG. 5c). This suggests that PAK activity is not limiting when oncogenic Ras is co-expressed in the cell. In order to determine if PAK3 acts through the phosphorylation of Raf-1 serine 338 or 339, constitutively active PAK3$[S91,A93,A95]$ was co-expressed with Raf-1$[A338]$ or Raf-1$[A339]$ and its ability to activate each mutant was measured (FIG. 5c). It was observed that PAK3$[S91,A93,A95]$ was capable of stimulating Raf-1$[A339]$ but not Raf-1$[A338]$ suggesting that PAK3 is regulating Raf-1 directly through serine 338. Finally, the in vivo phosphorylation of Raf-1 on serine 338 by PAK3 was confirmed immunologically using antibodies which specifically bind to Raf-1 phosphorylated on serine 338 (FIG. 5d). Raf-1 co-expressed in COS-7 cells with either Ras$[V12]$ or constitutively active PAK3$[S91,A93,A95]$ showed, respectively, 2.5 and 6.5-fold increases in the amount of phosphorylated serine 338.

Discussion

The fact that a dominant negative mutant of PAK3 interferes directly with Raf-1 activation demonstrates its essential role in the regulation of Raf-1 and consequently the MAPK signaling pathway. It is believed that all three mammalian isoforms of Raf can be regulated directly by PAK3 since the serine at Raf-1 residue 338 and the immediate N-terminal amino acids are completely conserved. PAK3 is believed to represent a novel point of cross-talk between the Ras/Raf and PAK signaling pathways. This cross-talk may ultimately play a critical role in the balance between cell survival and apoptosis. PAK3 may also provide an additional step of regulation providing balance between two distinct Ras effector pathways. The Rac guanine nucleotide exchange factors Vav and Sos have recently been shown to be activated by the Ras-dependent PI-3 kinase. A. S. Nimnual et al., *Science*, 279, 560 (1998); J. Han et al., *Science*, 279, 558 (1998). These exchange factors specifically control Rac activation and ultimately the Pak kinases, suggesting that the Ras/PI-3 kinase pathway may be capable of exerting broad control over the Ras/Raf pathway.

All publications, patents and patent applications mentioned in this specification are herein incorporated by reference to the same extent as if each individual publication, patent or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method to determine the ability of a test compound to alter PAK3 phosphorylation of Raf-1 comprising:
   (a) contacting a polypeptide that phosphorylates Raf-1 and which comprises the catalytic domain of PAK3 with the test compound in the presence of Raf-1 so as to activate Raf-1; and
   (b) correlating the extent of Raf-1 activation to the ability of the test compound to alter PAK3 phosphorylation of Raf-1.

2. The method of claim 1 wherein the ability of the test compound to inhibit PAK3 phosphorylation of Raf-1 is determined.

3. The method of claim 1 wherein activation of Raf-1 is measured in a cellular proliferation assay.

4. The method of claim 1 wherein said Raf-1 is Raf-1 CR3.

5. The method of claim 1 wherein said polypeptide is a recombinant PAK3.

6. The method of claim 2 wherein the ability of the test compound to inhibit PAK3 phosphorylation of Raf-1 is correlated to the ability of the test compound to inhibit pathological mammalian cellular proliferation.

7. The method of claim 6 wherein pathological mammalian proliferation is neoplastic cell growth.

8. The method of claim 1 wherein the polypeptide is contacted with an activated GTPase prior to contact with the test compound.

* * * * *

UNITED STATES PATENT AND TRADEMARK OFFICE
CERTIFICATE OF CORRECTION

PATENT NO. : 6,383,734 B1
DATED : May 7, 2002
INVENTOR(S) : Marshall et al.

It is certified that error appears in the above-identified patent and that said Letters Patent is hereby corrected as shown below:

Title page,
Item [56], OTHER PUBLICATIONS, insert -- Barnard, D., et al., "Oncogenes, Growth Factors and Phorbol Esters Regulate Raf-1 Through Common Mechanisms", *Oncogene*, 17, 1539-1547 (Sept. 1998). --.

Column 2,
Line 1, delete "8" and insert -- 268 --, therefor.

Column 4,
Line 31, delete "phosphoryl ate" and insert -- phosphorylate --, therefor.
Line 51, delete "PAK3 $^{[S91, S93, A95]}$" and insert -- PAK3 $^{[S91, A93, A95]}$ --

Column 5,
Line 24, delete "203 . 507" and insert -- 203-507 --, therefor.
Line 53, before "271" delete "5"

Column 11,
Line 42, delete "$_{33}$,RPRGQRDSSFFWEIE$_{345}$" and insert
-- $_{331}$RPRGQRDSS*FF*WEIE$_{345}$ -- , therefor.

Column 12,
Line 59, delete "(90 pg)" and insert -- (90 µg) --, therefor.

Signed and Sealed this

Twenty-fourth Day of December, 2002

JAMES E. ROGAN
*Director of the United States Patent and Trademark Office*